(12) United States Patent
Ralston et al.

(10) Patent No.: US 11,501,562 B2
(45) Date of Patent: Nov. 15, 2022

(54) ULTRASOUND FACE SCANNING AND IDENTIFICATION APPARATUSES AND METHODS

(71) Applicant: BFLY Operations, Inc., Guilford, CT (US)

(72) Inventors: Tyler S. Ralston, Clinton, CT (US); Jonathan M. Rothberg, Miami Beach, FL (US); Jianwei Liu, Fremont, CA (US)

(73) Assignee: BFLY OPERATIONS, INC., Guilford, CT (US)

( * ) Notice: Subject to any disclaimer, the term of this patent is extended or adjusted under 35 U.S.C. 154(b) by 205 days.

(21) Appl. No.: 16/859,124

(22) Filed: Apr. 27, 2020

(65) Prior Publication Data

US 2020/0349342 A1     Nov. 5, 2020

Related U.S. Application Data

(60) Provisional application No. 62/841,114, filed on Apr. 30, 2019.

(51) Int. Cl.
*G06V 40/16*     (2022.01)
*A61B 5/1171*   (2016.01)
(Continued)

(52) U.S. Cl.
CPC .......... *G06V 40/166* (2022.01); *A61B 5/1176* (2013.01); *A61B 5/6898* (2013.01);
(Continued)

(58) Field of Classification Search
CPC ........... G06K 9/00255; G06K 9/00288; G06K 2209/40; G01S 7/52004; G01S 7/539;
(Continued)

(56) References Cited

U.S. PATENT DOCUMENTS 9,067,779 B1    6/2015   Rothberg et al.
9,242,275 B2    1/2016   Rothberg et al.
(Continued)

OTHER PUBLICATIONS

Ridita, Development of an Ultrasound Based 3D Facial Scanning System, p. 1-3 (Year: 2014).*

(Continued)

*Primary Examiner* — Daniel L Murphy
*Assistant Examiner* — Amie M Ndure
(74) *Attorney, Agent, or Firm* — Osha Bergman Watanabe & Burton LLP

(57) ABSTRACT

An electronic face-identification device, which performs face scanning with ultrasonic waves, includes a housing and an ultrasound device disposed within the housing. The ultrasound device may be configured to transmit ultrasonic waves through air to a face and scan the face with the ultrasonic waves, to receive reflected waves through the air corresponding to reflections of the ultrasonic waves from the face, and to perform a recognition process for the face based on reflections of the ultrasonic waves from the face. The ultrasound device may include a plurality of ultrasound transducers, and electronic circuitry configured to transmit signals to the ultrasound transducers and receive signals from the ultrasound transducers. The face-identification device may be incorporated into various electronic equipment, such as hand-held equipment in the form of smartphones and tablet computers, as well as in larger scale installations at airports, workplace entryways, and the like.

18 Claims, 10 Drawing Sheets

(51) Int. Cl.
  *A61B 5/00* (2006.01)
  *G01S 7/52* (2006.01)
  *G01S 7/539* (2006.01)
(52) U.S. Cl.
  CPC .......... *G01S 7/52004* (2013.01); *G01S 7/539* (2013.01); *A61B 2560/0228* (2013.01); *A61B 2560/0462* (2013.01)
(58) Field of Classification Search
  CPC ................ A61B 5/6898; A61B 5/1176; A61B 2560/0228; A61B 2560/0462
  See application file for complete search history.

(56) References Cited

U.S. PATENT DOCUMENTS

| | | | |
|---|---|---|---|
| 9,521,991 B2 | 12/2016 | Rothberg et al. | |
| 9,592,030 B2 | 3/2017 | Rothberg et al. | |
| 10,303,932 B2* | 5/2019 | Wang | G06K 9/6215 |
| 10,624,613 B2 | 4/2020 | Ralson | |
| 10,650,273 B2* | 5/2020 | Wang | G06K 9/6215 |
| 2011/0055447 A1 | 3/2011 | Costa | |
| 2015/0032002 A1* | 1/2015 | Rothberg | A61B 8/483 600/440 |
| 2017/0285155 A1* | 10/2017 | Chen | G01S 7/5202 |
| 2017/0307741 A1 | 10/2017 | Ralston et al. | |
| 2018/0257927 A1 | 9/2018 | Rothberg et al. | |
| 2019/0001159 A1 | 1/2019 | Chen et al. | |
| 2019/0012525 A1* | 1/2019 | Wang | G06K 9/00295 |
| 2019/0182415 A1* | 6/2019 | Sivan | G06F 1/163 |
| 2019/0231312 A1 | 8/2019 | Fife et al. | |
| 2019/0275561 A1 | 9/2019 | Fife et al. | |
| 2019/0336099 A1 | 11/2019 | Fife et al. | |
| 2019/0336103 A1 | 11/2019 | Fife et al. | |
| 2019/0336104 A1 | 11/2019 | Fife et al. | |
| 2019/0370529 A1* | 12/2019 | Kumar | G06K 9/00275 |
| 2020/0013691 A1 | 1/2020 | Liu et al. | |
| 2020/0102214 A1 | 4/2020 | Liu et al. | |
| 2020/0147641 A1 | 5/2020 | Fife et al. | |
| 2020/0156110 A1 | 5/2020 | Miao et al. | |
| 2020/0184176 A1 | 6/2020 | Liu et al. | |
| 2020/0184177 A1 | 6/2020 | Liu et al. | |
| 2020/0239299 A1 | 7/2020 | Liu et al. | |
| 2020/0254487 A1 | 8/2020 | Miao et al. | |

OTHER PUBLICATIONS

Sumarang, Ultrasound Time Mapping based Human Face Identification System (Year: 2011).*

* cited by examiner

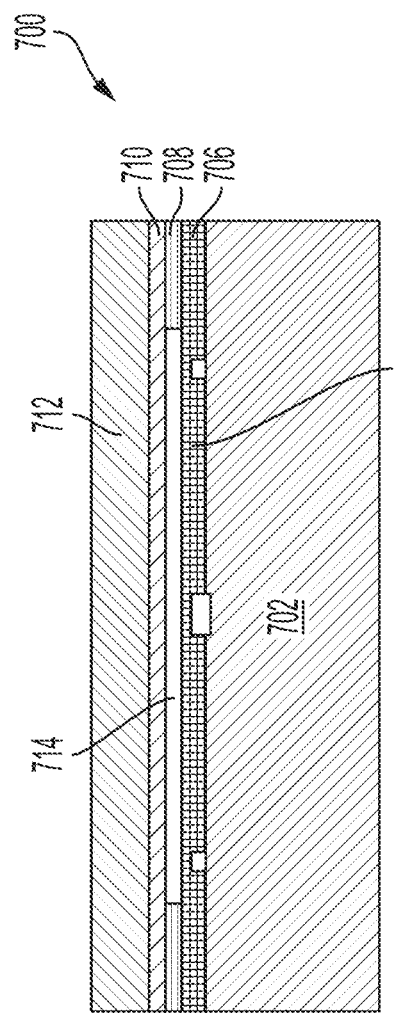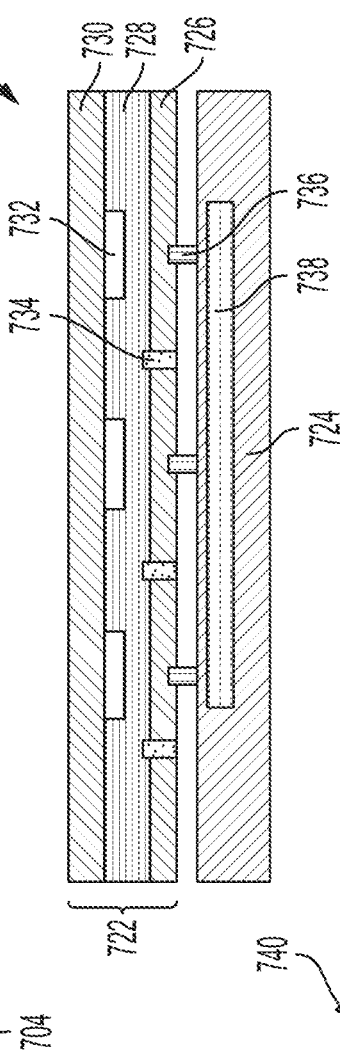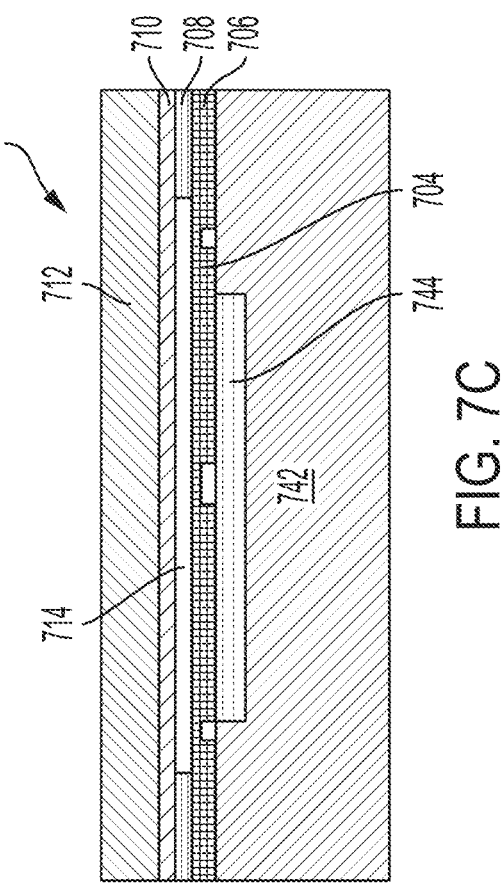
FIG. 7A
FIG. 7B
FIG. 7C

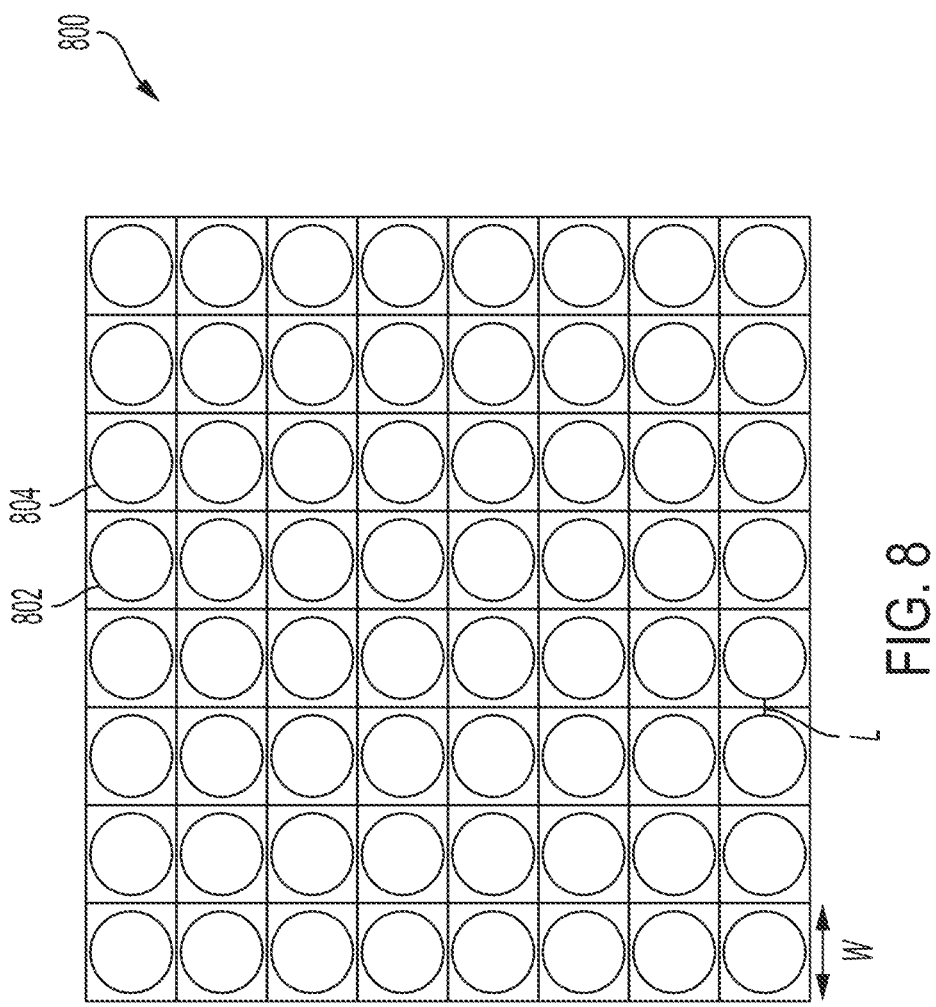

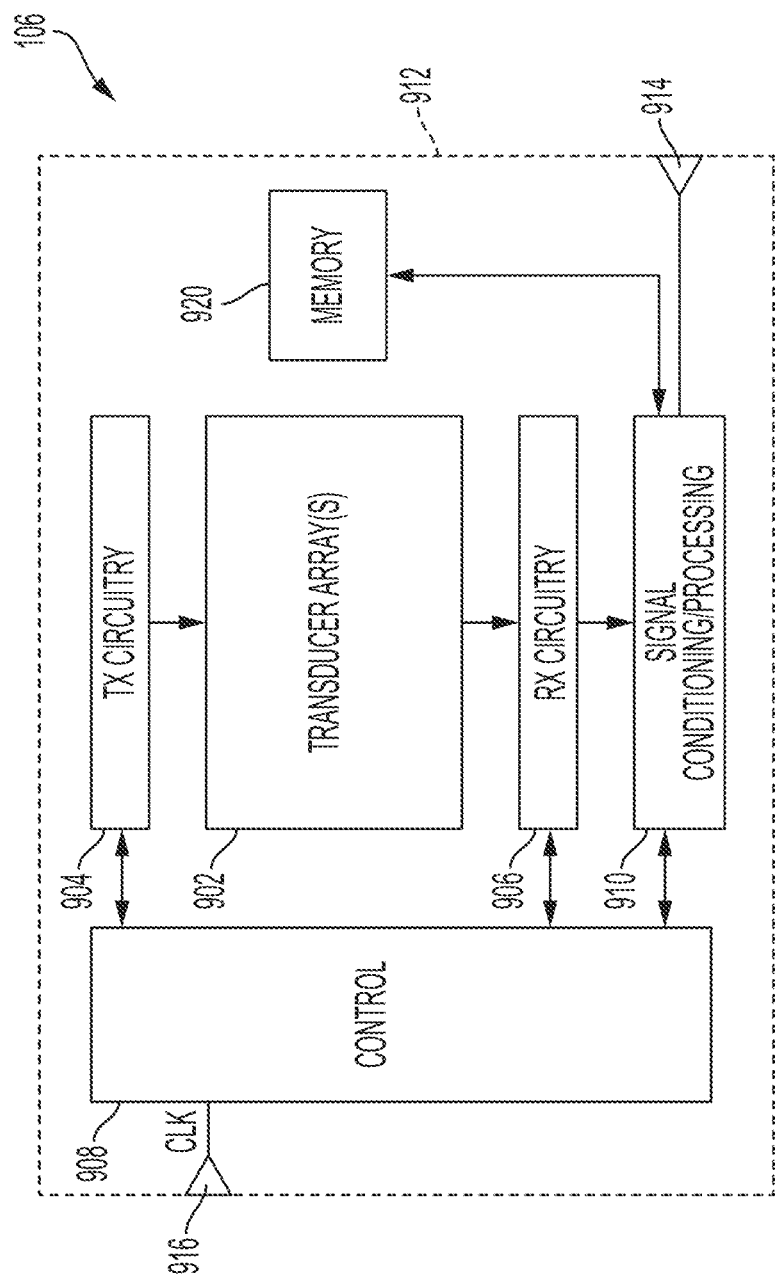

ULTRASOUND FACE SCANNING AND IDENTIFICATION APPARATUSES AND METHODS

CROSS-REFERENCE TO RELATED APPLICATION(S)

This application claims the benefit under 35 U.S.C. § 119(e) of U.S. Provisional Patent Application Ser. No. 62/841,114, filed Apr. 30, 2019, and entitled "ULTRASOUND FACE SCANNING AND IDENTIFICATION APPARATUSES AND METHODS," which is hereby incorporated herein by reference in its entirety.

FIELD OF THE DISCLOSURE

The present application relates generally to apparatuses and methods that use ultrasound imaging technology, and more specifically to apparatuses and methods that use ultrasound sensors to scan and identify a face.

BACKGROUND

Ultrasound systems may be used to perform diagnostic testing and imaging on an object, using acoustic or sound waves with frequencies that are higher than those audible to humans. Such testing and imaging may be performed non-destructively on the object. That is, the object need not undergo a physical transformation in order to be evaluated using ultrasonic sound waves. Sound waves classified as "ultrasonic" may have a frequency in a range of 20 kHz to 50 MHz.

When sound waves are transmitted into a body structure, such as that of a living mammal, at least some of the sound waves reflect off soft-tissue organs and other objects in the body structure, with different tissues and objects reflecting varying degrees of the sound waves. The reflected sound waves may be transformed into an electrical signal, which may then be recorded and displayed as an ultrasound image. The strength or amplitude of the reflected sound waves, and the delay or time it takes for the sound waves to travel to and reflect from the organs and other objects of the body structure, provide information that may be used to produce the ultrasound image. Different types of images can be formed using ultrasound technology. For example, images can be generated that show two-dimensional cross-sections of tissue, blood flow, motion of tissue over time, the location of blood, the presence of specific molecules, the stiffness of tissue, and the anatomy of a three-dimensional region.

Some ultrasound imaging devices may be fabricated using micromachined ultrasound transducers, which may include a flexible membrane suspended above a substrate. A cavity may be located between part of the substrate and the membrane, such that the combination of the substrate, the cavity, and the membrane may form a variable capacitor. When actuated by an appropriate electrical signal, the membrane may generate an ultrasound signal (i.e., ultrasonic waves) by vibration. Similarly, in response to receiving an ultrasound signal (i.e., ultrasonic waves), the membrane may vibrate and, as a result, may generate an electrical signal that in turn may be outputted for further processing.

SUMMARY OF THE DISCLOSURE

Ultrasound face scanning and identification apparatuses and methods are described. In some aspects of the present technology, an ultrasound device may be disposed within a housing and may be configured to scan a face with ultrasonic waves and to perform a recognition process for the face (i.e., facial recognition) based on reflections of the ultrasonic waves from the face. The ultrasound device may include an ultrasound-on-a-chip device having microfabricated ultrasound transducers integrated with electronic circuitry. The electronic circuitry may be integrated circuitry of a complementary metal oxide semiconductor (CMOS) substrate. The ultrasound device may be part of a portable electronic device (e.g., smartphone, tablet computer, laptop computer, etc.) for which face identification is desired periodically, or may be part of an installation that routinely performs face scanning and/or identification, such as, for example, for airport security screening, for motor-vehicle licensing operations, for workplace building-access screening, etc.

According to an aspect of the present technology, an electronic device able to perform face scanning and identification may be comprised of a housing and an ultrasound face-identification device disposed within the housing. The ultrasound face-identification device may be configured to scan a face with ultrasonic waves and to perform a recognition process for the face based on reflections of the ultrasonic waves from the face.

The ultrasound face-identification device may be comprised of a plurality of ultrasound transducers and electronic circuitry configured to transmit signals to the ultrasonic transducers and receive signals from the ultrasound transducers. For example, the ultrasound transducers may be integrated on a single semiconductor chip, and may be part of an ultrasound-on-a-chip device. The electronic circuitry also may be integrated on the single semiconductor chip as part of the ultrasound-on-a-chip device. Alternatively, the electronic circuitry may be disposed on at least one semiconductor chip separate from the single semiconductor chip.

The ultrasound face-identification device may be configured to transmit ultrasonic waves through air to the face. The ultrasound face-identification device also may be configured to receive reflected waves, which correspond to reflections of the ultrasonic waves transmitted through air and reflected from the face.

The electronic device may further be comprised of a memory device configured to store data of a reflection pattern corresponding to a person, or to store data of a plurality of reflection patterns corresponding to a plurality of persons. The electronic circuitry may be configured to compare the reflection pattern(s) stored in the memory device with a pattern corresponding to the reflected waves received by the ultrasound face-identification device.

According to another aspect of the present technology, a smartphone device able to perform ultrasound face scanning and identification may be comprised of a housing and an ultrasound device disposed within the housing. The ultrasound device may be configured to scan a face of a user with ultrasonic waves, and to perform a recognition process based on reflections of the ultrasonic waves from the face. The ultrasound device may be comprised of a plurality of ultrasound transducers and electronic circuitry configured to transmit signals to the ultrasound transducers and receive signals from the ultrasound transducers. The electronic circuitry may control the ultrasound transducers to perform a sector scan of the face, to perform a plurality of sector scans of the face to produce a 3D scan, or to perform an area scan of the face to produce a 3D scan.

The ultrasound transducers may be configured to transmit ultrasonic waves through air to the face. The ultrasound transducers also may be configured to receive reflected waves through air, with the reflected waves corresponding to reflections of the ultrasonic waves transmitted through air and reflected from the face.

The smartphone device may further be comprised of a memory device configured to store data of a reflection pattern corresponding to the user. The electronic circuitry may be configured to compare the reflection pattern stored in the memory device with a pattern corresponding to the reflected waves received by the ultrasound device, to determine whether the user is authorized to access restricted functions of the smartphone.

According to a further aspect of the present technology, an ultrasound identification method may be comprised of: scanning a face using ultrasonic waves transmitted from ultrasound transducers of an electronic device, with the ultrasonic waves being transmitted through air to the face; receiving reflected waves through air, with the reflected waves corresponding to the ultrasonic waves transmitted through air and reflected from the face; and comparing a pattern corresponding to the reflected waves to a stored reflection pattern corresponding to a known face. The stored reflection pattern may be obtained from a memory device of the electronic device.

The scanning may involve utilizing ultrasound transducers configured to operate in at least one frequency range selected from: 50 kHz to 100 kHz, 100 kHz to 200 kHz, 200 kHz to 300 kHz, 300 kHz to 400 kHz, and 400 kHz to 500 kHz.

The scanning may involve performing a sector scan of the face, or performing a plurality of sector scans of the face to produce a 3D scan, or performing an area scan of the face to produce a 3D scan.

The electronic device may be a portable electronic device having a display screen. The scanning may involve transmitting the ultrasonic waves through the display screen. The ultrasound identification method may further be comprised of performing a calibration operation to determine transmission and reception artifacts due to irregularities of the display screen. The irregularities may be comprised of one or both of: surface irregularities of the display screen, and internal irregularities of a material forming the display screen. Based on the calibration operation, the method may further be comprised of compensating for the irregularities by controlling one or both of a phase and a timing of an ultrasonic wave emitted from individual ones of the ultrasound transducers, to cause ultrasonic waves having uniform wavefronts to be transmitted to the face. Also, based on the calibration operation, the method may be comprised of compensating for the irregularities by correcting the reflected waves received from the face.

BRIEF DESCRIPTION OF THE DRAWINGS

Various aspects and embodiments of the application will be described with reference to the following figures. It should be appreciated that the figures are not necessarily drawn to scale. Items appearing in multiple figures may be indicated by the same reference number in some or all of the multiple figures in which they appear.

FIGS. 7A, 7B, and 7C illustrate cross-sectional view of capacitive micromachined ultrasound transducers (CMUTs) according to various embodiments of the present technology.

FIG. 8 illustrates an array of ultrasound transducers according to an embodiment of the present technology.

FIG. 9 illustrates an arrangement of components of an ultrasound face-identification device according to an embodiment of the present technology.

DETAILED DESCRIPTION

Figure 1:
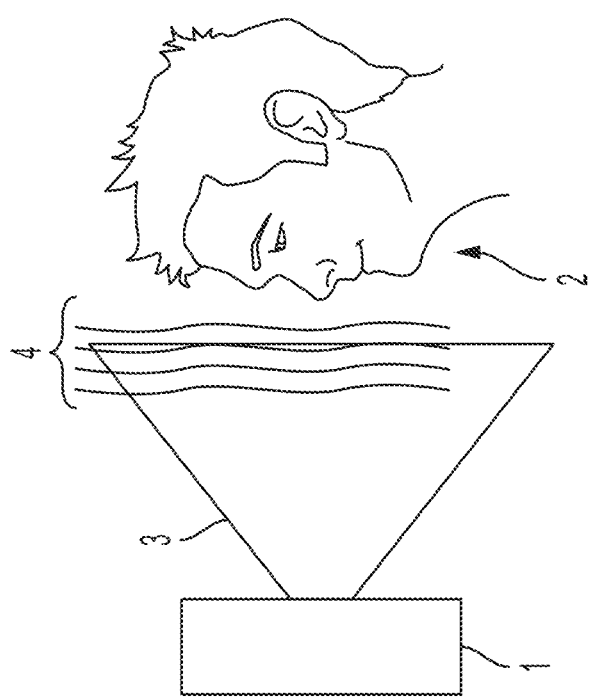
FIG. 1 illustrates a view of an electronic device utilizing ultrasonic waves to identify a face, according to an embodiment of the present technology.

Ultrasound face scanning and identification apparatuses and methods are described. In some aspects of the present technology, an ultrasound face-identification device may be disposed within a housing and may be configured to scan a face with ultrasonic waves and to perform an identification process for the face based on reflections of the ultrasonic waves from the face.

The ultrasound face-identification device may include an ultrasound-on-a-chip device having microfabricated ultrasound transducers integrated with electronic circuitry on a single chip. The electronic circuitry may be integrated circuitry of a CMOS substrate.

The ultrasound face-identification device may be part of a portable or hand-held electronic device, such as a smartphone, a tablet computer, a laptop computer, and the like, for which face identification is desired periodically, such as for authentication purposes, for example. Alternatively, the ultrasound face-identification device may be part of an installation that routinely performs face scanning and/or identification, such as for airport security screening, for motor-vehicle licensing operations, and for workplace building-access screening, for example.

Exterior surface characteristics of a solid object may be evaluated using ultrasonic waves. When acoustic or sound waves are launched or transmitted to a solid object, at least some of the sound waves may reflect off the object's outer or exterior surfaces. (The terms "external" and "exterior" may be used interchangeably herein. The terms "internal" and "interior" may be used interchangeably herein.) The strength or amplitude of the sound waves reflected from one or more of the exterior surfaces, and the delay or time it takes for the sound waves to travel to and reflect or echo from the exterior surface(s), may be used to obtain information about the object's exterior surface(s), such as an overall exterior shape of the object. Also, information may be obtained about variations in density and/or other physical characteristics of the object's exterior surface(s) (e.g., scar tissue), which may manifest as variations in reflection characteristics of the sound waves that reflect from the exterior surface(s).

Ultrasonic waves may be produced using a transducer (ultrasound transducer) manufactured using known microfabrication techniques. For example, the ultrasound transducer may include a flexible membrane suspended above a cavity in a substrate, forming a variable capacitor. When actuated by an appropriate electrical signal, the membrane may generate ultrasonic waves by vibration. These sound waves may be launched toward an object to be imaged and/or tested, and reflected sound waves may cause the membrane of the ultrasound transducer (or a membrane of a different ultrasound transducer) to vibrate. The vibrations may be transformed into an electrical signal for imaging or further testing.

The object may be a face of a person (e.g., "Person A"), and acoustic reflection characteristics of the face may be used to determine an identity of the person. In other words, the acoustic reflection characteristics from the face may be used to determine that Person A corresponds to the face.

Pulses of ultrasonic sound waves launched toward a face may give rise to a specific echo or acoustic reflection pattern corresponding to sound waves that reflect off the face. Facial features such as cheekbone shape, location and shape of eye(s), shape and height of nose, etc., may be unique to each person and thus the pattern of sound waves reflected from the face may be used to identify the person to whom the face belongs.

For example, the reflection pattern determined for a face may be compared with a stored reflection pattern for a known person, such as an owner of a smartphone having ultrasound face-identification functionality. The reflection pattern may be used to authenticate that a user of the smartphone as its owner, and to enable access to restricted smartphone applications. That is, when the stored reflection pattern corresponding to the owner of the smartphone device is determined to match the reflection pattern of the face of the user of the smartphone device, then the restricted smartphone applications may be unlocked.

In another example, the reflection pattern obtained from Person B's face may be compared with stored reflection patterns in a database corresponding to a known group of employees of a company. The reflection pattern from Person B's face may be used to confirm whether Person B may gain access to the company's workplace premises (e.g., a building or a room in a building). That is, when one of the stored reflection patterns is determined to match the reflection pattern from the face of Person B, then Person B may be given entry to the workplace premises.

In a further example, the reflection pattern obtained from Traveler C's face may be compared with stored reflection patterns in a database corresponding to a known group of people. The reflection pattern from Traveler C's face may be used to confirm whether Traveler C may gain access to a transportation vehicle (e.g., a train, an airplane, a ship, etc.). That is, the stored reflection patterns may be for people with restricted travel privileges. When one of the stored reflection patterns is determined to match the reflection pattern from Traveler C's face, then Traveler C may be denied entry to the transportation vehicle.

In another example, the reflection pattern obtained from Driver D's face may be compared with stored reflection patterns in a database corresponding to a state's licensed drivers. The reflection pattern from Driver D's face may be used to confirm whether Driver D is one of the licensed drivers of the state if, for example, Driver D is involved in an automobile incident.

The presence of cosmetics or makeup can mask facial features in an optical image of a face. For example, when imaged optically, a person's nose may appear narrower than in reality, or the person's cheekbones may appear higher than in reality. That is, through the use of creatively applied shadowing makeup, optical illusions may be created that cause an optical image of the person's face to be different from the person's face in reality. This is because an optical image of a face provides two-dimensional information about the face. Depth information (e.g., information on the height of the tip of the nose relative to the height of the base of the nose) is not easily or reliably obtained from an optical image of the face. Optical images therefore are flawed vehicles for performing face identification.

In contrast to information obtainable from conventional optical images, information obtainable from scanning a face with ultrasonic waves may yield three-dimensional data on the scanned face, such as the relative heights of various features of the face. That is, because there is a time component involved in the transmission of ultrasonic waves to a face, and the reflection of the ultrasonic waves from various surfaces of the face, the time component (e.g., time delay) may be used to determine distance and hence height of the various surfaces of the face.

The presence of facial hair can mask facial features in an optical image of a face. For example, when imaged optically, a mustache may mask the shape of a person's lip area, and a beard may mask the shape of a person's jaw area. When a significant portion of the face is obscured by facial hair, optical images cannot be used reliably for performing face identification.

In contrast, although ultrasonic waves launched toward a face may experience some attenuation from facial hair before reaching the surfaces of the face, and although reflections of the ultrasonic waves may face some attenuation from the facial hair after reflecting from the surfaces of the face, scanning a face with ultrasonic waves may yield sufficient data to enable three-dimensional determination of the relative heights of various features of the face. Therefore, for identification purposes, scanning a face with ultrasonic waves may yield three-dimensional data that is more reliable than what is possible with conventional, two-dimensional optical imaging. This may be especially true when combined with other traditional face identification approaches, such as 2D and 3D optical topographical mapping with structured illumination or multi-view stereo computer-vision techniques, and/or Fourier/principal component analysis (PCA) of 2D optical images.

According to an embodiment of the present technology, an electronic device may be comprised of a housing and an ultrasound device disposed within the housing. The ultrasound device may be configured to scan a face with ultrasonic waves and to perform a recognition process for the face based on reflections of the ultrasonic waves from the face.

In an aspect of the embodiment, the ultrasound device may be comprised of a plurality of ultrasound transducers and electronic circuitry configured to transmit signals to the ultrasound transducers and receive signals from the ultrasound transducers. The ultrasound transducers may be integrated on one chip. For example, the ultrasound device may be an ultrasound-on-a-chip device in which the ultrasound transducers are integrated on a single semiconductor chip.

In an aspect of the embodiment, the ultrasound device may be an ultrasound-on-a-chip device in which the ultrasound transducers and the electronic circuitry are integrated on the single semiconductor chip.

Alternatively, in an aspect of the embodiment, the electronic circuitry may be disposed on at least one semiconductor chip separate from the ultrasound transducers.

In an aspect of the embodiment, the ultrasound device may be configured to transmit ultrasonic waves through air to the face, and to receive reflected waves through air. The reflected waves may correspond to the reflections of the ultrasonic waves transmitted through air and reflected from the face.

In an aspect of the embodiment, the electronic device may be further comprised of a memory device configured to store data of a reflection pattern corresponding to a person, or to store data of a plurality of reflection patterns corresponding to a plurality of persons. The electronic circuitry may be configured to compare a reflection pattern corresponding to the reflected waves received by the ultrasound device to the reflection pattern(s) stored in the memory device.

In an aspect of the embodiment, the electronic device may be further comprised of a transmitter configured to transmit a pattern corresponding to the reflected waves to an external processor. The external processor may operate to determine whether the pattern corresponding to the reflected waves matches a pattern stored in an external memory device coupled to the processor. Optionally, the electronic device may be further comprised of a receiver configured to receive information on whether the pattern corresponding to the reflected waves matches a pattern stored in the external memory device.

this higher frequency range, the spatial resolution may be in the range of approximately 0.7 mm to 1.1 mm. However, in this higher frequency range, attenuation of ultrasonic waves in air may be approximately 35 dB/m.

The electronic circuitry may be configured to enable a user to select an operating frequency within a selected one of the frequency ranges. For example, the electronic circuitry may be configured to control the ultrasound transducers to perform an initial lower-resolution scan at a relatively lower frequency of one frequency range and a subsequent higher-resolution scan at a relatively higher frequency of another frequency range.

As will be appreciated, there are tradeoffs between frequency, resolution, and attenuation. For situations where ultrasonic waves need not travel very far to reach a face to be scanned (e.g., when the face is within about 6 inches to 12 inches of a smartphone incorporating an ultrasound device according to various embodiments of the present technology), then higher frequencies may be more desirable because attenuation of the ultrasonic waves in air is not a significant concern due to the short transit distance to and from the face. On the other hand, for situations where ultrasonic waves need to travel relatively longer distances to reach a face to be scanned (e.g., when the face is a few feet from an installation incorporating an ultrasound device according to various embodiments of the present technology), then lower frequencies may be more desirable because attenuation of the ultrasonic waves may cause difficulty in obtaining a reliable scan of the face.

TABLE 1 includes data that may be relevant in choosing a frequency range for scanning a face.

TABLE 1

| Acoustic Frequency | 50 kHz to 100 kHz | 100 kHz to 200 kHz | 300 kHz to 500 kHz |
|---|---|---|---|
| Timing Resolution | 10 µs to 20 µs | 5 µs to 10 µs | 2.0 µs to 3.3 µs |
| Phase Resolution | ~1.5 cm | ~1 cm | ~0.5 cm |
| Attenuation in Air | ~1.2 dB/m | ~3 dB/m | ~35 dB/m |
| Wavelength ($\lambda$) | ~3.4 mm to 6.9 mm | ~1.7 mm to 3.4 mm | ~700 µm to 1.1 mm |
| Transducer Diameter | ~1.5 mm to 2.5 mm | ~1.1 mm to 1.2 mm | ~560 µm to 600 µm |
| Spacing Between Transducers ($\lambda/2$ to $\lambda$) | ~2.5 mm to 5 mm | ~1 mm to 2 mm | ~500 µm to 1 mm |
| Transducer Membrane Thickness | ~20 µm | ~10 µm | ~10 µm |

In an aspect of the embodiment, the ultrasound transducers may be configured to operate in one frequency range or a plurality of frequency ranges. The frequency range(s) may be selectable and may be comprised of any one or any combination of: a 50 kHz to 100 kHz range, a 100 kHz to 200 kHz range, a 200 kHz to 300 kHz range, a 300 kHz to 400 kHz range, a 400 kHz to 500 kHz range. A frequency range may be selected based on a type of face scan to be performed (e.g., fine scan of detailed features, coarse scan of general features, etc.) and/or an environment in which a face scan is to be performed (e.g., temperature, humidity, etc.).

For example, when attenuation of ultrasonic waves in air may be a concern, a lower frequency range of 50 kHz to 100 kHz may be selected for the ultrasonic waves. In this lower frequency range, with the speed of sound in air taken to be 343 m/s, attenuation of ultrasonic waves in air may be approximately 1.2 dB/m. However, in this frequency range, the spatial resolution may be in the range of approximately 3 mm to 7 mm.

In another example, when attenuation of ultrasonic waves in air may not be a concern, a higher frequency range of 300 kHz to 500 kHz may be selected for the ultrasonic waves. In In an aspect of the embodiment, the electronic circuitry may control the ultrasound transducers to perform a sector scan of the face, or to perform a plurality of sector scans of the face to produce a three-dimensional (3D) scan. A sector scan may be analogous to a B-scan used in medical ultrasound imaging, where a trace or line is scanned along the face to obtain a "slice" of information about the face. For example, a vertical sector scan may be performed near a centerline of the face, to capture reflections from facial features such as the forehead, the nose, the lips, and the chin. Multiple sector scans along the face may be combined to yield a 3D scan, yielding depth information in addition to two-dimensional position information. With this aspect of the embodiment, the ultrasound transducers may be arranged in a one-dimensional array or line, and may be controlled to emit ultrasonic waves in unison.

In an aspect of the embodiment, the electronic circuitry may control the ultrasound transducers to perform an area scan of the face to produce a 3D scan. With this aspect of the embodiment, the ultrasound transducers may be arranged in a two-dimensional array and may be controlled to emit ultrasonic waves in unison, in subgroups, or individually.

The phases and launch or firing times of the ultrasound transducers may be individually controlled by the electronic circuitry so that the ultrasonic waves have desired wavefront characteristics. For example, the phases may be controlled so that the wavefront has a desired angle relative to the face. Optionally, the ultrasound transducers may be individually controlled to control their phases and launch times in order to compensate for irregularities in, for example, a display screen through which the ultrasonic waves must travel, as discussed below.

According to an embodiment of the present technology, an electronic device may be comprised of a housing and an ultrasound device disposed within the housing. The housing may include a display screen. The ultrasound device may be configured to scan a face with ultrasonic waves and to perform a recognition process for the face based on reflections of the ultrasonic waves from the face. For example, the ultrasound device may be configured to scan the face by transmitting ultrasonic waves through the display screen.

In an aspect of the embodiment, the ultrasound device may be comprised of an array of ultrasound transducers facing toward an internal surface of the display screen, and electronic circuitry coupled to the array to transmit signals to the ultrasound transducers and receive signals from the ultrasound transducers. The array may be a one-dimensional arrangement of the transducers or a two-dimensional arrangement of the ultrasound transducers.

In an aspect of the embodiment, the electronic circuitry may be configured to control the ultrasound transducers to perform a calibration operation to determine transmission and reception artifacts due to irregularities of the display screen. The irregularities may be comprised of surface irregularities of the display screen and/or internal irregularities of a material forming the display screen. Based on the calibration operation, the electronic circuitry may compensate for the irregularities by controlling one or both of a phase and a launch time of an ultrasonic wave emitted from individual ones of the ultrasound transducers, to cause ultrasonic waves having, for example, a uniform wavefront to be transmitted to the face. As will be appreciated, other types of wavefronts may be used, including non-uniform wavefronts. Optionally, based on the calibration operation, the electronic circuitry may compensate for the irregularities by correcting the signals received from the ultrasonic transducers. ultrasound According to an embodiment of the present technology, a smartphone that performs ultrasound face identification may be comprised of a housing and an ultrasound device disposed within the housing. The ultrasound device may be configured to scan a face of a user with ultrasonic waves and to perform an identification process based on reflections of the ultrasonic waves from the face.

In an aspect of the embodiment, the ultrasound device may be comprised of a plurality of ultrasound transducers and electronic circuitry configured to transmit signals to the ultrasound transducers and receive signals from the ultrasound transducers. The electronic circuitry may be configured to control the ultrasound transducers to perform a sector scan of the face. Optionally, the electronic circuitry may be configured to control the ultrasound transducers to perform a plurality of sector scans of the face, to produce a 3D scan. In another option, the electronic circuitry may be configured to control the ultrasound transducers to perform an area scan of the face, to produce a 3D scan.

In an aspect of the embodiment, the ultrasound transducers may be configured to transmit ultrasonic waves through air to the face, and to receive reflected waves through air. The reflected waves may correspond to the reflections of the ultrasonic waves transmitted through air and reflected from the face.

In an aspect of the embodiment, the smartphone may be further comprised of a memory device configured to store data of a reflection pattern corresponding to the user. The electronic circuitry may be configured to compare the reflection pattern stored in the memory device with a pattern corresponding to the reflected waves received by the ultrasound device, to determine whether the user is authorized to access restricted functions of the smartphone.

In an aspect of the embodiment, the ultrasound transducers may be configured to operate in one frequency range or a plurality of frequency ranges. The frequency range(s) may be selectable and may be comprised of: a 50 kHz to 100 kHz range, a 100 kHz to 200 kHz range, a 200 kHz to 300 kHz range, a 300 kHz to 400 kHz range, and a 400 kHz to 500 kHz range.

In an aspect of the embodiment, the ultrasound transducers may be comprised of multiple subsets of transducers. The transducers of one subset may be different from the transducers of another subset. For example, the transducers of one subset may have a relatively smaller spacing between transducers, and the transducers of another subset may have a relatively larger spacing between transducers. Each frequency range of the ultrasound device may utilize a different subset of the ultrasound transducers, although some of the ultrasound transducers may belong to more than one of the subsets.

According to an embodiment of the present technology, a smartphone that performs ultrasound face identification may be comprised of a housing and an ultrasound device disposed within the housing. The housing may be comprised of a display screen. The ultrasound device may be configured to scan a face of a user with ultrasonic waves and to perform a recognition process based on reflections of the ultrasonic waves from the face. For example, the ultrasound device may be configured to scan the face by transmitting ultrasonic waves through the display screen.

In an aspect of the embodiment, the ultrasound device may be comprised of an array of ultrasound transducers facing toward an internal surface of the display screen, and electronic circuitry coupled to the array to transmit signals to the ultrasound transducers and receive signals from the ultrasound transducers. For example, the array may be a one-dimensional arrangement of the ultrasound transducers, or may be a two-dimensional arrangement of the ultrasound transducers.

In an aspect of the embodiment, the electronic circuitry may be configured to control the ultrasound transducers to perform a calibration operation to determine transmission and reception artifacts due to irregularities of the display screen. The irregularities may be comprised of surface irregularities of the display screen and/or internal irregularities of a material forming the display screen. Based on the calibration operation, the electronic circuitry may compensate for the irregularities by controlling one or both of a phase and a timing of an ultrasonic wave emitted from individual ones of the ultrasound transducers, to cause ultrasonic waves having a desired wavefront to be transmitted to the face. The desired wavefront may have a uniform shape or may have a non-uniform shape. Optionally, based on the calibration operation, the electronic circuitry may compensate for the irregularities by correcting the signals received from the ultrasound transducers.

According to an embodiment of the present technology, an ultrasound identification method may be comprised of:

scanning a face using ultrasonic waves transmitted from ultrasound transducers of an electronic device, with the ultrasonic waves being transmitted through air to the face; receiving reflected waves through air, with the reflected waves corresponding to the ultrasonic waves transmitted through air and reflected from the face; and comparing a pattern corresponding to the reflected waves to a stored reflection pattern corresponding to a known face.

In an aspect of the embodiment, the stored reflection pattern may be obtained from a memory device of the electronic device.

In an aspect of the embodiment, the scanning may involve utilizing ultrasound transducers configured to operate in one or more frequency ranges. The frequency range(s) may be selectable and may be any one or a combination of: a 50 kHz to 100 kHz range, a 100 kHz to 200 kHz range, a 200 kHz to 300 kHz range, a 300 kHz to 400 kHz range, and a 400 kHz to 500 kHz range.

In an aspect of the embodiment, the scanning may involve performing a sector scan of the face, performing a plurality of sector scans of the face to produce a 3D scan, or performing an area scan of the face to produce a 3D scan.

In an aspect of the embodiment, the electronic device may be a portable electronic device, and the scanning may involve transmitting the ultrasonic waves through a display screen of the portable electronic device.

In an aspect of the embodiment, the electronic device may be incorporated in an installation that performs ultrasound face scans routinely.

In an aspect of the embodiment, the method may be further comprised of performing a calibration operation to determine transmission and reception artifacts due to irregularities of the display screen. The irregularities may be comprised of surface irregularities of the display screen and/or internal irregularities of a material forming the display screen.

In an aspect of the embodiment, the method may be further comprised of, based on the calibration operation, compensating for the irregularities by controlling one or both of a phase and a timing of an ultrasonic wave emitted from individual ones of the ultrasound transducers to cause ultrasonic waves having uniform wavefronts to be transmitted to the face. Optionally, the method may be further comprised of, based on the calibration operation, compensating for the irregularities by correcting the reflected waves received from the face.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Turning now to the figures, FIG. 1 is a schematic view of an electronic device 1 that utilizes ultrasound technology to identify a face 2. The electronic device 1 scans the face 2 by transmitting ultrasonic waves 3 toward the face 2. Reflected waves 4, which are ultrasonic waves that reflect off the face 2 towards the electronic device 1, are received by the electronic device 1. An electrical signal corresponding to the reflected waves 4 contains data specific to the face 2. The electrical signal may be used to perform a recognition process for identifying the face 2.

Figure 2B:
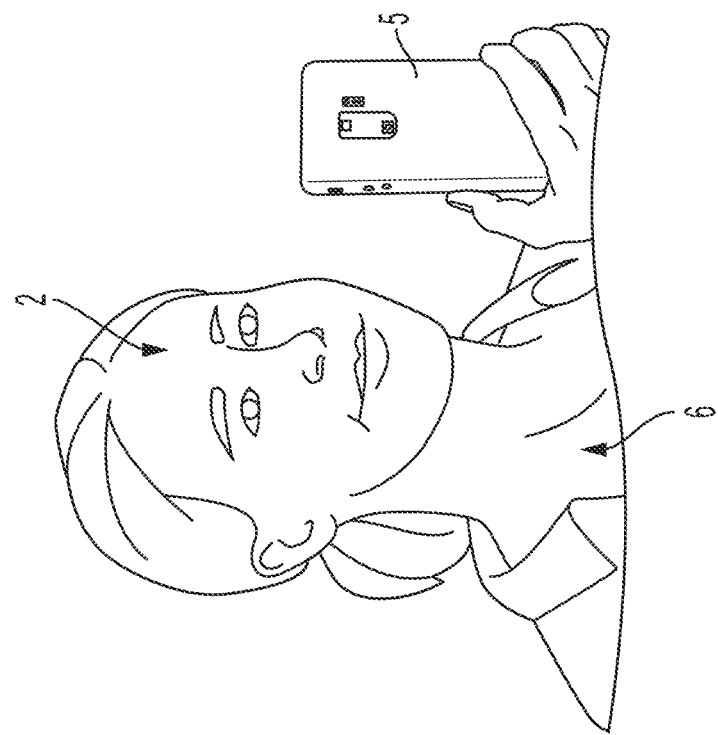
FIGS. 2A and 2B show views of a smartphone that may be used to identify a face using ultrasonic waves, according to an embodiment of the present technology.
Figure 2A:
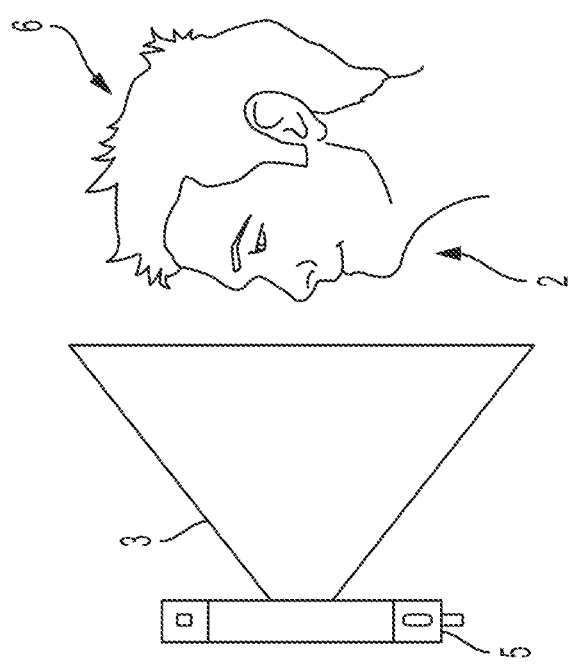

In an embodiment of the present technology, the electronic device 1 may be incorporated as part of a portable electronic apparatus, such as a smartphone, a tablet computer, a laptop computer, and the like, for which face identification is desired periodically, such as for authentication purposes to unlock the electronic apparatus or to unlock functions of the apparatus. FIGS. 2A and 2B schematically show examples of this embodiment, in which the electronic device 1 (not visible in the figure) is incorporated in a smartphone 5. The smartphone 5 may be held by a user 6 to scan the face 2 of the user 6 for authentication purposes.

Figure 3B:
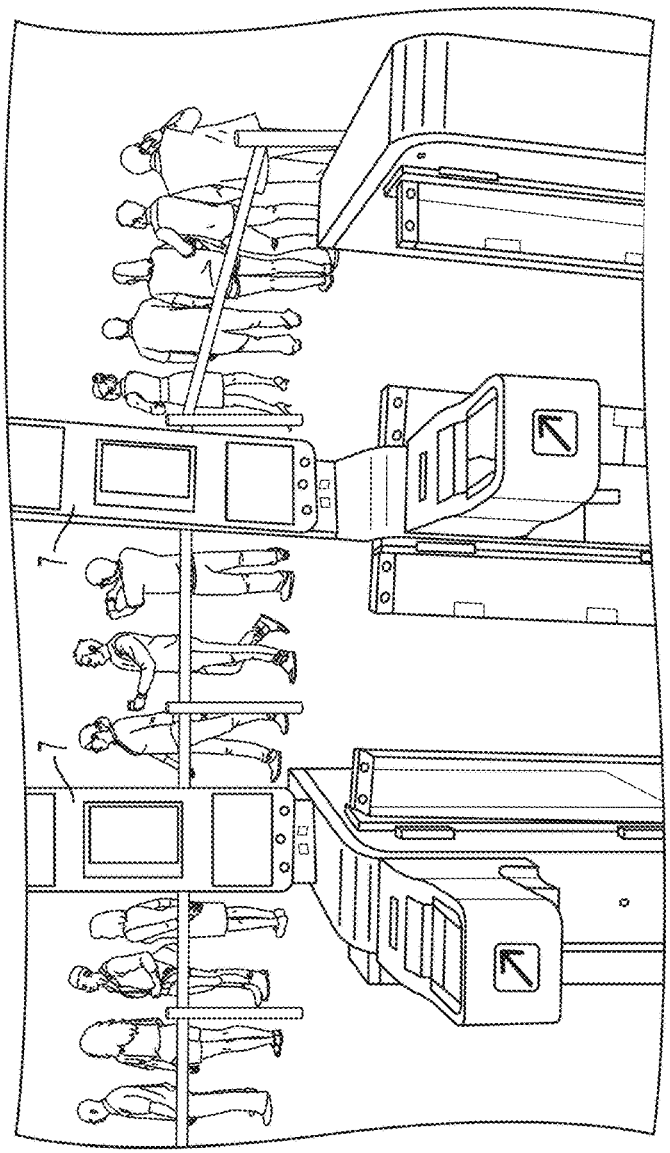
FIGS. 3A and 3B show views of an installation that may be used to identify a face using ultrasonic waves, according to an embodiment of the present technology.
Figure 3A:
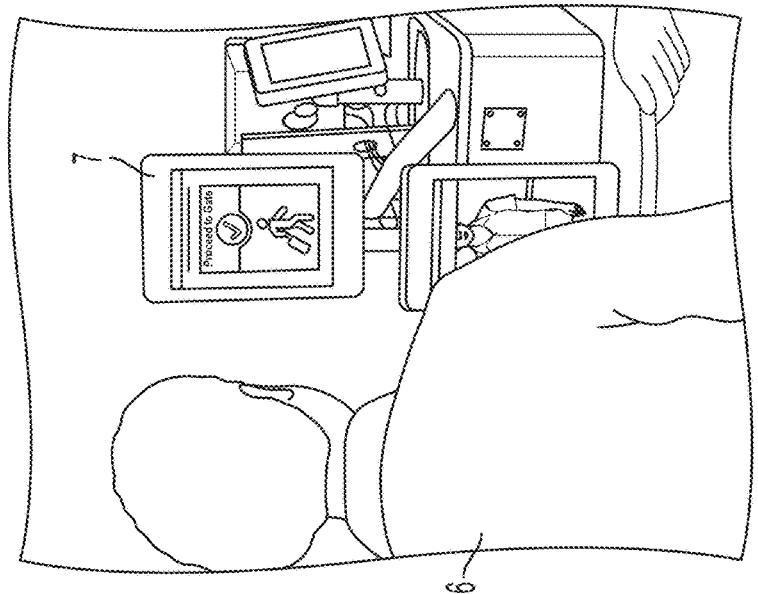
Figure 4B:
FIGS. 4A and 4B show views of another installation that may be used to identify a face using ultrasonic waves, according to an embodiment of the present technology.
Figure 4A:
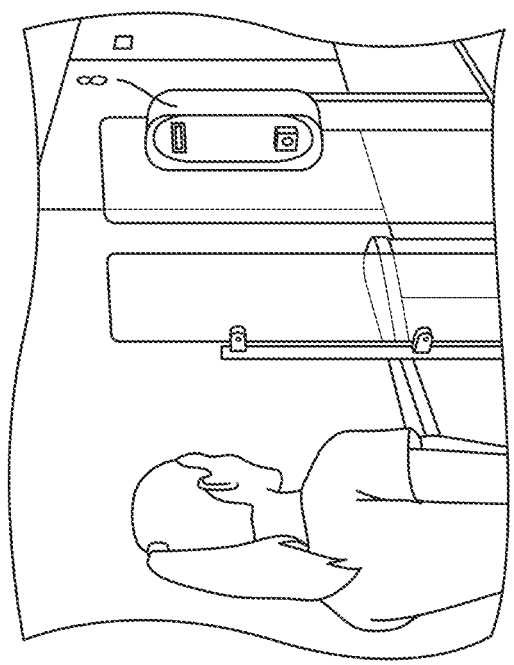

In another embodiment of the present technology, the electronic device 1 may be incorporated as part of an installation that routinely performs face scanning and/or identification. Such an installation may be used for airport security screening, for obtaining information for motor-vehicle licenses, and for workplace building-access screening, for example. FIGS. 3A and 3B schematically show examples of this embodiment, in which the installation is a screening station 7 at an airport. FIGS. 4A and 4B schematically show other examples of this embodiment, in which the installation is a building-access screener 8 or an entryway screener 9. The electronic device 1 (not visible in the figures) may be incorporated in the screening station 7, the building-access screener 8, and the entryway screener 9 to perform face scanning and/or identification on many different faces routinely.

Figure 5B:
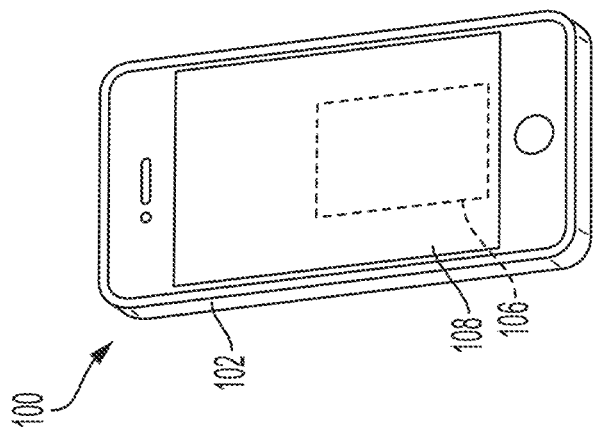
FIG. 5B illustrates an assembled view of the electronic device of FIG. 5A.
Figure 5A:
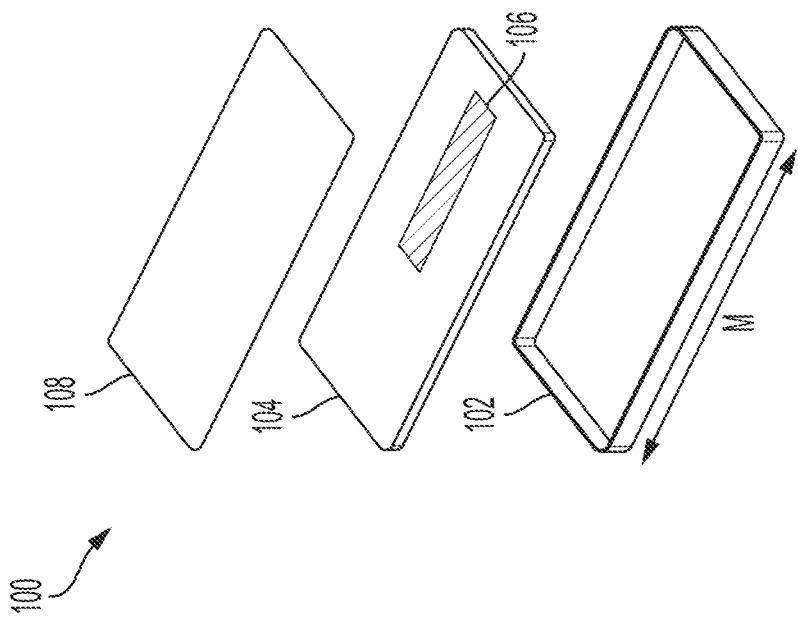
FIG. 5A illustrates an exploded view of an electronic device according to an embodiment of the present technology.

FIG. 5A schematically illustrates an exploded view of a portable electronic device 100 according to an embodiment of the present technology. The portable electronic device 100 may include a housing 102, a circuit board 104, an ultrasound face-scanning device 106 disposed on and electrically connected to the circuit board 104, and a cover 108.

The electronic device 100 may be a smartphone or other portable electronic device. The electronic device 100 may be sized to be hand-held, for instance having a long dimension M of less than approximately six inches. The various aspects described herein are not limited by the particular dimensions. The electronic device 100 may include electronic circuitry that provides various functions, such as making and receiving phone calls, sending and receiving text messages, connecting to the Internet, taking pictures, word processing, speech recognition, and/or other functions.

The housing 102 may be configured to house the circuit board 104. The circuit board 104 may be a printed circuit board in some embodiments, although alternatives are possible. More generally, the circuit board 104 is one non-limiting example of a substrate that may be used to support various components of the electronic device 100.

The ultrasound transducers of the ultrasound face-scanning device 106 may be an array of capacitive micromachined ultrasound transducers (CMUTs), which may be integrated with complementary metal oxide semiconductor (CMOS) electronic circuitry on a single semiconductor chip as part of an ultrasound-on-a-chip device, as mentioned above. Alternatively, the ultrasound transducers may be disposed on a separate chip from the electronic circuitry. As shown in FIG. 5A, the ultrasound face-scanning device 106 may be a discrete packaged component electrically coupled to the circuit board 104. Other configurations are possible, however, such as monolithically integrating the ultrasound transducers of the ultrasound face-scanning device 106 with other components on a common substrate.

The cover 108 is configured to mate with the housing 102 and define an enclosed space in which the circuit board 104 is disposed. The cover 108 may be formed of a layer of glass, or plastic, or another material that permits transmission of ultrasonic waves. The cover 108 may form part of a display component of the electronic device 100. For example, the cover 108 may be formed of glass, and an organic display layer may be disposed on a backside of the glass of the cover 108, an example of which is described further below. The ultrasound face-scanning device 106 may be configured to emit and receive ultrasound signals (i.e., ultrasonic waves) through the glass of the cover 108. In this manner, a face may be scanned with the ultrasonic waves, and reflections of the ultrasonic waves from the face may be received and processed. In some embodiments, the ultrasound face-scanning device 106 may be configured to emit and receive through glass, ceramic, metal, and/or organic film stacks, such as may be present in smartphones, tablet computers, and other electronic devices.

FIG. 5B shows an assembled view of the electronic device 100 of FIG. 5A. In this figure the electronic device 100 is a smartphone, and the cover 108 is a display component of the smartphone (e.g., a touchscreen display). The ultrasound face-scanning device 106, which is disposed within an enclosed space defined by the housing 102 and the cover 108, is illustrated as a dashed box because it is not visible through the cover 108.

As mentioned above, the ultrasound face-scanning device 106 may be comprised of a plurality of ultrasound transducers. Additionally, the ultrasound face-scanning device 106 may be comprised of electronic circuitry configured to transmit signals to the ultrasound transducers and receive signals from the ultrasound transducers. The ultrasound transducers may be integrated on a single semiconductor chip, and the electronic circuitry may be integrated on the same single semiconductor chip as the ultrasound transducers, as part of an ultrasound-on-a-chip device. Alternatively, the electronic circuitry may instead be provided on one or more semiconductor chip(s) separate from the ultrasound transducers.

The ultrasound face-scanning device 106 may be configured to emit ultrasonic waves to outside of the cover 108, and to receive reflected waves, which for example may be reflected from a face positioned opposite the cover 108 or nearly opposite the cover 108. As will be appreciated, the face must be located within a distance such that even with attenuation of the ultrasonic waves in air, the reflected waves provide an electrical signal sufficient to further face-identification processing. The electronic circuitry may include processing circuitry configured to compare a reflection pattern of the reflected waves to one or more patterns stored in a memory device housed in the housing 102. If the processing circuitry determines that there is a match between the reflection pattern of the reflected waves and a pattern stored in the memory, the processing circuitry may enable a restricted function of the electronic device 100 to be activated.

It should be appreciated that the electronic device 100 of FIGS. 5A and 5B may include additional components not illustrated. For example, the electronic device 100 may be part of a smartphone, and the circuit board 104 may include a processor, a memory device, a microphone, a speaker, a camera, a display driver, and/or other components of the smartphone. Thus, the electronic device 100 may perform functions other than face scanning. In fact, the electronic device 100 may be used, in some embodiments, primarily for functions other than face scanning. When the electronic device 100 is a smartphone, the face-scanning functionality may be used, for example, to provide a user with access to additional smartphone functions, such as payment functions, camera functions, and other known smartphone functions.

Although not separately illustrated, in an embodiment of the present technology, the ultrasound face-scanning device 106 may be incorporated, in whole or in part, in a housing of an installation instead of the housing 102 of the electronic device 100. The ultrasound transducers of the ultrasound face-scanning device 106 may be positioned in the installation to emit ultrasonic waves toward a face positioned opposite or near a predetermined part of the installation, and to receive reflected waves, which reflect from the face. The electronic circuitry of the ultrasound face-scanning device 106 may be positioned in the installation or may be located external to the installation. For example, if the installation is one of a group of similar installations at a facility (e.g., an airport), the electronic circuitry may be part of an external server that receives and processes signals from multiple installations at the facility. In this embodiment, a reflection pattern corresponding to reflected waves from a face at one of the installations may be compared with a database of patterns stored in a memory device operatively connected to the external server. For example, the database of patterns may correspond to faces of people with travel restrictions. If processing by the external server determines that there is a match between the reflection pattern for the face at one of the installations and a pattern in the database stored in the memory, the external server may issue a notification to personnel at that installation to warn them that the face undergoing identification processing belongs to someone who has travel restrictions.

Figure 6:
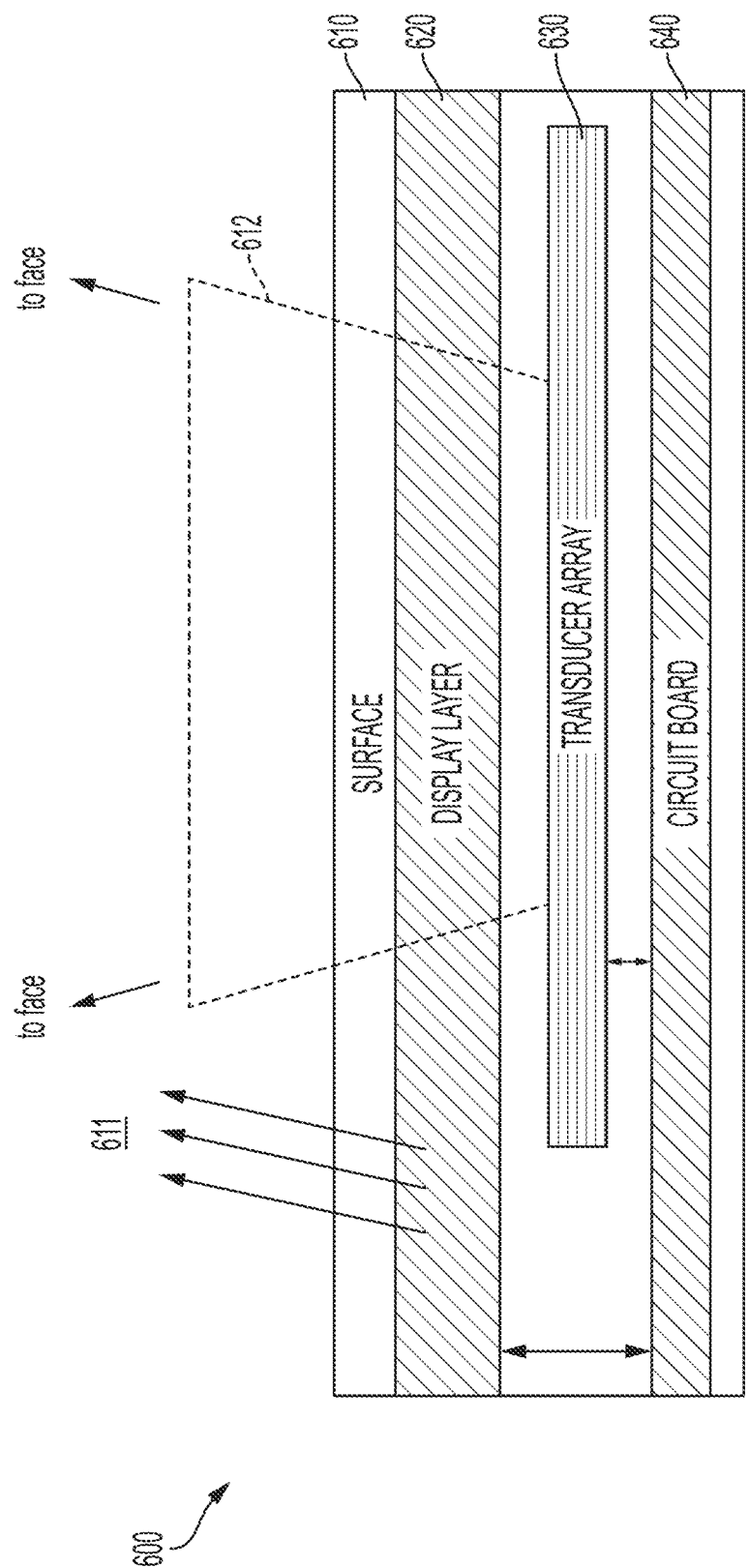
FIG. 6 illustrates a cross-sectional view of a portion of a smartphone according to an embodiment of the present technology.

FIG. 6 schematically illustrates an example of a cross-section of a portion of a smartphone having face-scanning functionality, according to an embodiment of the present technology. The smartphone 600 may be comprised of a circuit board 640 electrically coupled to, and configured to control, a display layer 620 and an array 630 of ultrasound transducers. The display layer 620 may be configured to produce light 611 through a surface 610, which may be comprised of a transparent material. For example, the transparent material may be a glassy material or a polymeric material. The display layer 620 may be comprised a light-emitting diode (LED) display, or an organic light-emitting diode (OLED) display, or another type of display known in the art. The array 630 may be configured to emit ultrasonic waves 612, and may be comprised of any number of ultrasound transducers arranged in a layer.

As noted above, the ultrasound transducers may be configured to operate in a predetermined frequency range or in a frequency range selected from a plurality of frequency ranges. The frequency range(s) may be comprised of any one or a combination of: a 50 kHz to 100 kHz range, a 100 kHz to 200 kHz range, a 200 kHz to 300 kHz range, a 300 kHz to 400 kHz range, a 400 kHz to 500 kHz range. Depending on the frequency range in operation, some of the ultrasound transducers may controlled to emit ultrasonic waves, while others of the ultrasound transducers may be controlled to be non-operational or to receive but not transmit ultrasonic waves. That is, the array 630 of ultrasound transducers may be comprised of sub-arrays (not shown), with each of the sub-arrays configured to operate in a frequency range different from that of another one of the sub-arrays.

As has been described herein, aspects of the present technology may utilize capacitive micromachined ultrasound transducers (CMUTs). Various configurations of ultrasound transducers and electronic circuitry for controlling the ultrasound transducers and/or processing signals from the ultrasound transducers ("control and processing circuitry") may be employed. Three non-limiting examples include: (a) an array of CMUTs disposed on a semiconductor substrate separate from the control and processing circuitry; (b) an array of CMUTs formed of an engineered substrate and integrated with a circuitry substrate; and (c) an array of CMUTs directly integrated on a circuitry substrate through low temperature wafer bonding of a membrane layer on the integrated circuit substrate. Each of these examples is now described.

FIG. 7A illustrates a non-limiting example of a CMUT 700 that may be used in an ultrasound face-scanning device, according to various embodiments of the present technology. As will be described further below, the illustrated CMUT 700 does not include control or processing circuitry. Thus, an array of such transducers on one semiconductor chip may be coupled to a separate chip or circuit board having suitable control and/or processing circuitry.

The CMUT 700 is comprised of a substrate 702, an electrode 704, dielectric layers, 706, 708, 710, and a silicon layer 712. The combination of the dielectric layer 710 and the silicon layer 712 may serve as a membrane above a cavity 714. The silicon layer 712 may be doped suitably to be conducting, or an optional further electrode layer (not shown) may be disposed on the silicon layer 712. Thus, the combination of the membrane, the cavity 714, and the electrode 704 may form a variable capacitor, with the capacitance depending on the distance between the membrane and the electrode 704.

The substrate 702 may be any suitable substrate. For example, the substrate 702 may be a semiconductor substrate formed of silicon or another suitable semiconductive material. As described previously, although the substrate 702 may include the electrode 704 and electrical routing layers (not shown), it may lack control circuitry and processing circuitry for controlling operation of the CMUT 700 and for processing output signals from the CMUT 700. Instead, such circuitry may be provided off-chip.

The electrode 704 may be of any material and/or shape, and may have any dimension(s) for providing desired electrical behavior, including applying a voltage and receiving a signal resulting from vibration of the membrane. In some embodiments, the electrode 704 may be shaped as a ring, and thus may appear in cross-section as shown in FIG. 7A. However, other shapes are possible. The electrode 704 may be formed of a metal or other suitable conductive material.

The dielectric layers 706, 708, 710 may be formed of any suitable material(s) exhibiting dielectric behavior. As a non-limiting example, the dielectric layer 706 may be aluminum oxide ($Al_2O_3$), and the dielectric layers 708, 710 may be silicon oxide.

The silicon layer 712 may have any suitable thickness for serving as a membrane, or part of a membrane in combination with the dielectric layer 710. For example, the membrane, including the silicon layer 712, may have a thickness less than 50 μm in some embodiments.

As described above, an alternative implementation is to form the CMUT as part of an engineered substrate that is bonded to an integrated-circuit substrate with electronic circuitry. The electronic circuitry of the integrated-circuit substrate may include circuitry representing control circuitry and/or processing circuitry, such as depicted in FIG. 7B. Specifically, FIG. 7B is a cross-sectional view of an example of a plurality of CMUTs 720 that include a circuitry substrate integrated with an engineered substrate having sealed cavities, according to an embodiment of the present technology.

As shown in FIG. 7B, the CMUTs 720 include an engineered substrate 722 and a circuitry substrate 724. The engineered substrate 722 includes a first silicon layer 726, a dielectric layer 728, and a second silicon layer 730 representing a membrane. Cavities 732 are positioned between the dielectric layer 728 and the second silicon layer 730. The cavities 732 are sealed by the second silicon layer 730 in this example. The engineered substrate 722 is further comprised of insulating portions 734 providing electrical insulation between conductive portions of the first silicon layer 726.

The circuitry substrate 724 includes integrated circuitry 738, which may include control circuitry and/or processing circuitry for controlling operation of the CMUTs 720 and/or for processing signals output from the CMUTs 720. In some embodiments, the integrated circuitry 738 is CMOS circuitry and the circuitry substrate 724 is a CMOS substrate. The integrated circuitry 738 may control the CMUTs 720 to emit and receive in a manner such that for a single transmit event, multiple transducers of the CMUTs 720 may emit and receive ultrasound signals. In some embodiments, multi-channel emission and reception may be performed as part of a given transmit event, providing greater data than single-channel transmission and reception would. For example, multi-channel operation for a given a transmit event may facilitate correction of aberrations or other undesirable effects in the data. In some embodiments, the integrated circuitry 738 may include multiplexing circuitry. For example, the multiplexing circuitry may be configured to multiplex transmission or reception of multiple channels.

The engineered substrate 722 and the circuitry substrate 724 may be bonded together by bonds 736. In some embodiments, the bonds 736 may be conductive, providing electrical connection between the engineered substrate 722 and the integrated circuitry 738.

The CMUTs 720 may be formed using two wafer-level bonding steps. The engineered substrate 722 may be formed by bonding a first silicon wafer with a second silicon wafer, and then annealing at high temperature to form a strong bond. The annealing temperature may be above 450° C. in some embodiments. The engineered substrate 722 may subsequently be bonded with the circuitry substrate 724 at a temperature sufficiently low to ensure that the integrated circuitry 738 is not damaged by heat during the subsequent bonding.

Further examples of CMUTs formed in an engineered substrate and bonded with a circuitry substrate are described in U.S. Pat. Publication No. 2018/0257927 A1, which is hereby incorporated herein by reference in its entirety.

An alternative implementation, a CMUT 740 may be formed directly on an integrated-circuit substrate by bonding a membrane of the CMUT 740 directly to an integrated-circuit substrate, as schematically illustrated in FIG. 7C. As shown, the CMUT 740 has a structure that is substantially the same as that of the CMUT 700 of FIG. 7A, except that the substrate 702 is replaced with an integrated-circuit substrate 742, which includes integrated circuitry 744. The integrated circuitry 744 may be substantially the same as the integrated circuitry 738 of FIG. 7B, and in some embodiments may perform the same functions.

The CMUT 740 of FIG. 7C may be fabricated using low-temperature wafer bonding. Various structures of the integrated-circuit substrate 742 may be fabricated, including the cavity 714. Subsequently, a wafer comprised of the dielectric layer 710 and the silicon layer 712 may be bonded with the integrated-circuit substrate 742 to seal the cavity 714. The bonding may be performed at a temperature sufficiently low to ensure that the integrated circuitry 744 is not damaged. For example, the bonding may be performed at temperatures at or below 450° C. in some embodiments.

Further examples of CMUTs integrated with an integrated-circuit substrate, and having a membrane bonded directly with the integrated-circuit substrate, are described in U.S. Pat. No. 9,242,275, which is incorporated herein by reference in its entirety.

According to various embodiments of the present technology, an ultrasound face-scanning device may employ an array of CMUTs. For example, an array of the types of CMUTs shown in FIGS. 7A-7C may be used. FIG. 8 schematically illustrates an example of an array. As will be appreciated, other types of arrays may be used.

FIG. 8 shows an example of a plan view of a two-dimensional array 800 of ultrasound transducers 802. The ultrasound transducers 802 may be any of the types previously described in connection with FIGS. 7A-7C, although other forms of CMUTs may be used. In the illustrated example, the ultrasonic sound transducers 802 are circular and separated into transducer cells 804. The cells 804 may have a width W in a range of 10 µm to 100 µm, or 25 µm to 100 µm, or 50 µm to 75 µm, or any other suitable range of dimensions for providing a resolution sufficient to detect facial features. The ultrasound transducers 802 may be spaced by a distance L, which may be between 1 µm and 20 µm. The membrane of one or more of the cells 804 may have a thickness (into and out of the page) between 1 µm and 20 µm in some embodiments, and between 1 µm and 5 µm in other embodiments. The ultrasound transducers 802 may have a pitch of any suitable value, such as within the range of values for W.

The ultrasound transducers 802 may have dimensions sufficient to operate at any one of the following frequency ranges, or any combination of the following frequency ranges: a 50 kHz to 100 kHz range, a 100 kHz to 200 kHz range, a 200 kHz to 300 kHz range, a 300 kHz to 400 kHz range, and a 400 kHz to 500 kHz range. Although the ultrasound transducers 802 of the array 800 are shown to be arranged in a two-dimensional array, which is suitable for some embodiments, for other some other embodiments the ultrasound transducers 802 may be arranged in a line, i.e., in a one-dimensional array. When arranged in a two-dimensional array, the array may have any suitable number of ultrasound transducers 802 along rows and columns of the array. In some embodiments, the array may have an equal number of transducers in rows and columns, however alternatives are possible. According to embodiments of the present technology, the ultrasound transducers 802 may transmit and/or receive ultrasound signals of frequencies assuming any value or range of values within those ranges listed above.

FIG. 9 schematically illustrates an example of the ultrasound face-scanning device 106, which embodies various aspects of the technology described herein. The ultrasound face-scanning device 106 may include a transducer array 902, a transmitter 904 (TX circuitry), a receiver 906 (RX circuitry), a controller 908, a signal processor 910, and a memory device 920. In FIG. 9, the illustrated components are shown to be located on a single circuit board 912; however, in various other embodiments, one or more of the illustrated components may instead be located off-board. It should be appreciated that communication between one or more of the illustrated components may be performed in any of numerous ways, e.g., via one or more high-speed busses for high-speed intra-board communication and/or communication with one or more off-board components.

The transducer array 902 may take on any of numerous forms, and aspects of the present technology do not necessarily require the use of any particular type(s) or arrangement(s). An ultrasound transducer of the array 902 may, for example, include CMUT, a CMOS ultrasonic transducer (CUT), a piezoelectric micromachined ultrasonic transducer (PMUT), and/or another suitable ultrasound transducer. The array 902, the transmitter 904, and the receiver 906 may be formed on separate chips. Alternatively, a combination of the array 902 and some or all of the other components shown in FIG. 9 may be integrated on the same chip in an ultrasound-on-a-chip device. Information regarding microfabricated ultrasound transducers may be found in U.S. Pat. No. 9,067,779, which is incorporated by reference herein in its entirety.

The controller 908 may generate timing and control signals that are used to synchronize and coordinate operation of other components of the ultrasound face-scanning device 106. For example, the controller 908 may provide a scan-control signal to the transmitter 904 to control generation and outputting of drive pulses by the transmitter 904 to the transducer array 902, to cause the ultrasound transducers of the transducer array 902 to emit pulses of ultrasonic waves to a face. The controller 908 may be driven by a clock signal CLK supplied to an input port 916 of the ultrasound face-scanning device 106. The drive pulses from the transmitter 904 may drive the ultrasound transducers of the transducer array 902 individually or collectively.

Reflected waves, which are reflected from surfaces of a face being scanned, may impinge on the transducer array 902, causing the ultrasound transducers of the transducer array 902 to vibrate and output analog electrical signals representing vibration data. The receiver 906 may generate digital electrical signals from the vibration data obtained from the transducer array 902, and may provide the digital electrical signals to the signal processor 910. The signal processor 910 may process the electrical signals from the receiver 906 to generate a reflection pattern.

Figure 10B:
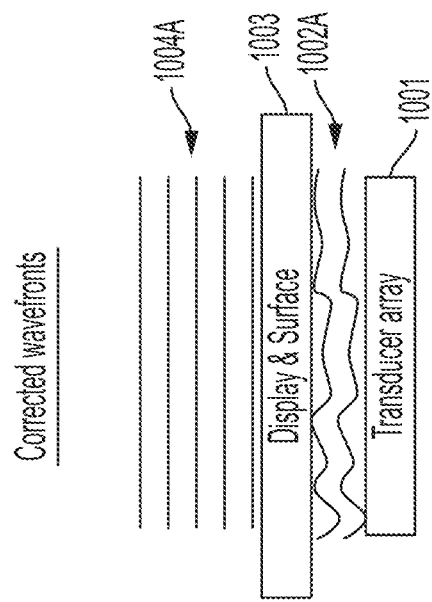
FIGS. 10A and 10B illustrate a calibration procedure according to an embodiment of the present technology.
Figure 10A:
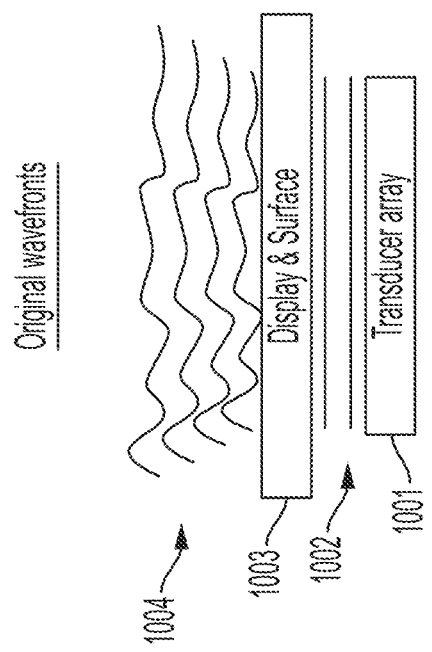

FIGS. 10A and 10B schematically illustrate calibration operations that may be used to correct for irregularities in the transmission and/or reception of ultrasonic waves. The irregularities may be caused by, for example, irregularities at the surface 610 of a display screen and/or internal irregularities of a material forming a display layer 620 of the display screen (see FIG. 6). As will be appreciated, other sources of irregularities may be possible.

As shown in FIG. 10A, ultrasonic waves emitted from a transducer array 1001 may have an initial wavefront 1002 that is uniform in shape, represented by the straight parallel lines in the figure. After passing through a display screen ("display & surface"), the ultrasonic waves may have an altered wavefront 1003 that is non-uniform in shape. Such non-uniformity in the altered wavefront 1003 results in the ultrasonic waves reaching a face non-uniformly. That is, some portions of the altered wavefront 1003 may be delayed in reaching the face due to irregularities in the display screen, which could produce distortions in the resulting reflection pattern. By determining the shape of the altered wavefront 1003 and then controlling the phases and the launch or firing times of the ultrasound transducers of the transducer array 1001, the irregularities may be compensated.

As shown in FIG. 10B, by controlling the ultrasound transducers of the transducer array 1001 to produce ultrasonic waves having an inverted wavefront 1002A, the ultrasonic waves emanating from the display screen 1003 have a corrected wavefront 1004A that has known shape (e.g., a uniform shape). Consequently, because the corrected wavefront 1004A has a known uniform shape, subsequent processing of reflected waves from the face is less prone to distortion due to the irregularities.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

The term "substantially" if used herein may be construed to mean within 95% of a target value in some embodiments, within 98% of a target value in some embodiments, within 99% of a target value in some embodiments, and within 99.5% of a target value in some embodiments. In some embodiments, the term "substantially" may equal 100% of the target value.

Any reference to a numerical value being between two endpoints, if such a reference is made herein, should be understood to encompass a situation in which the numerical value can assume either of the endpoints. For example, stating that a characteristic has a value between A and B, or between approximately A and B, should be understood to mean that the indicated range is inclusive of the endpoints A and B unless otherwise noted.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Some aspects of the present technology may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An electronic device, comprising:
   a display screen; and
   an ultrasound device, further comprising:
      an array of ultrasound transducers that faces an internal surface of the display screen;
      electronic circuitry that is coupled to the array, wherein the electronic circuitry transmits signals to and receives signals from the ultrasound transducers such that the electronic device electronically scans ultrasonic waves over a face and performs facial recognition based on reflections of the ultrasonic waves from the face.

2. The electronic device of claim 1, further comprising: a housing, wherein
   the ultrasound device is disposed within the housing.

3. The electronic device of claim 2, wherein the ultrasound device is an ultrasound-on-a-chip device.

4. The electronic device of claim 3, wherein:
   the ultrasound transducers operate in a plurality of frequency ranges, and
   the electronic circuitry enables a user to select an operating frequency within a selected one of the plurality of frequency ranges.

5. The electronic device of claim 4, wherein the electronic circuitry controls the ultrasound transducers to perform an initial lower-resolution scan at a relatively lower frequency and a subsequent higher-resolution scan at a relatively higher frequency.

6. The electronic device of claim 2, wherein the ultrasound device:
   transmits the ultrasonic waves, through air, to the face, and
   receives, through the air, the reflections of the ultrasonic waves from the face.

7. The electronic device of claim 6, further comprising:
   a memory device that stores a reflection pattern corresponding to a known face of a person; and
   electronic circuitry that compares the reflection pattern stored in the memory device to a pattern corresponding to the reflections received by the ultrasound device.

8. The electronic device of claim 6, wherein
   the ultrasound device comprises a transmitter that transmits a pattern, corresponding to the reflections, to an external processor coupled to an external memory device, and
   the ultrasound device determines whether the pattern corresponding to the reflections matches a pattern stored in the external memory device.

9. The electronic device of claim 2, wherein
   the electronic device is a smartphone device, and
   the ultrasound device is an ultrasound-on-a-chip device.

10. The electronic device of claim 9, further comprising:
    a memory device that stores a reflection pattern corresponding to a user; and
    electronic circuitry that compares the reflection pattern stored in the memory device to a pattern corresponding to the reflections received by the ultrasound device, wherein
    the electronic circuitry determines whether the user is authorized to access restricted functions of a processor of the smartphone device.

11. The electronic device of claim 9, wherein the ultrasound device operates in at least one frequency range selected from a group consisting of:
    50 kHz to 100 kHz,
    100 kHz to 200 kHz,
    200 kHz to 300 kHz,
    300 kHz to 400 kHz, and
    400 kHz to 500 kHz.

12. The electronic device of claim 1, wherein the electronic circuitry controls the ultrasound transducers to perform a calibration operation that determines transmission and reception artifacts due to irregularities of the display screen.

13. The electronic device of claim 12, wherein the irregularities include one or both of:
surface irregularities of the display screen, and
internal irregularities of a material forming the display screen.

14. The electronic device of claim 12, wherein, based on the calibration operation, the electronic circuitry compensates for the irregularities by controlling one or both of a phase and a timing of an ultrasonic wave emitted from one or more of the ultrasound transducers such that ultrasonic waves that have uniform wavefronts are transmitted to the face.

15. The electronic device of claim 12, wherein, based on the calibration operation, the electronic circuitry compensates for the irregularities by correcting the signals received from the ultrasound transducers.

16. An electronic device, comprising:
a housing; and
an ultrasound device that is an ultrasound-on-a-chip device, comprising:
ultrasound transducers; and
electronic circuitry that transmits signals to and receives signals from the ultrasound transducers,
wherein
the ultrasound device electronically scans ultrasonic waves over a face and performs facial recognition based on reflections of the ultrasonic waves from the face,
the ultrasound device is disposed within the housing,
the housing comprises a display screen,
the ultrasound device scans the face by transmitting ultrasonic waves through the display screen, and
the electronic circuitry controls the ultrasound transducers to perform a calibration operation that determines transmission and reception artifacts due to irregularities of the display screen.

17. The electronic device of claim 16, wherein, based on the calibration operation, the electronic circuitry compensates for the irregularities by controlling one or both of a phase and a timing of an ultrasonic wave emitted from one or more of the ultrasound transducers such that ultrasonic waves that have uniform wavefronts are transmitted to the face.

18. The electronic device of claim 16, wherein, based on the calibration operation, the electronic circuitry compensates for the irregularities by correcting the signals received from the ultrasound transducers.

* * * * *